(12) United States Patent
Hoffman et al.

(10) Patent No.: US 7,974,377 B2
(45) Date of Patent: Jul. 5, 2011

(54) X-RAY DETECTION METHODS AND APPARATUS

(75) Inventors: David Michael Hoffman, New Berlin, WI (US); Jeffrey Alan Kautzer, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 553 days.

(21) Appl. No.: 11/523,359

(22) Filed: Sep. 19, 2006

(65) Prior Publication Data

US 2008/0069298 A1 Mar. 20, 2008

(51) Int. Cl.
*A61B 6/00* (2006.01)
(52) U.S. Cl. .................................................. 378/19

(58) Field of Classification Search ............... 378/4–20; 250/370.08, 370.09
See application file for complete search history.

(56) References Cited

U.S. PATENT DOCUMENTS

| | | | |
|---|---|---|---|
| 5,223,717 A | 6/1993 | Charpak | 250/374 |
| 6,421,412 B1 | 7/2002 | Hsieh et al. | 378/9 |
| 7,016,455 B2 | 3/2006 | Bruder et al. | 378/9 |
| 7,019,303 B2 | 3/2006 | Homme et al. | 250/370.11 |
| 7,039,153 B2 | 5/2006 | Bruder et al. | 378/9 |
| 2003/0123718 A1* | 7/2003 | Edic et al. | 382/131 |
| 2004/0109532 A1* | 6/2004 | Ford et al. | 378/57 |

* cited by examiner

*Primary Examiner* — Courtney Thomas
(74) *Attorney, Agent, or Firm* — Ziolkowski Patent Solutions Group, SC

(57) ABSTRACT

A method includes inserting a first x-ray detector between a second x-ray detector and an object.

14 Claims, 2 Drawing Sheets

US 7,974,377 B2

X-RAY DETECTION METHODS AND APPARATUS

BACKGROUND OF THE INVENTION

This invention relates generally to diagnostic imaging methods and apparatus, and more particularly, to methods and apparatus that provide for handling of received x-rays.

Computed tomography (CT) systems sold today exclusively utilize x-ray systems that operate in a non Energy Discrimination mode as embodied by individual x-ray counting along with the measurement of each x-ray's energy. Some systems try to accomplish tissue differentiation through dual KVP scanning or with layered integrating detectors.

Improvements in the art are available as described below.

BRIEF DESCRIPTION OF THE INVENTION

In one aspect, a method includes inserting a first x-ray detector between a second x-ray detector and an object.

In another aspect, apparatus includes a first computed tomography detector configured to be inserted between an object to be scanned and a curvilinear computed tomography detector.

In yet another aspect, a system includes an x-ray source, a first x-ray detector positioned to receive x-rays emitted from the source, and a second x-ray detector positioned to receive x-rays emitted from the source and the second x-ray detector positioned in front of the first x-ray detector such that the second x-ray detector at least partially blocks x-rays from impinging the first x-ray detector.

In still yet another aspect, a method includes scanning a patient such that heart data is received in a first detector and non-heart data is received in a second detector different than the first.

In yet still another aspect, a method includes performing a scan of a heart in a single rotation of a CT gantry.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

Figure 1:
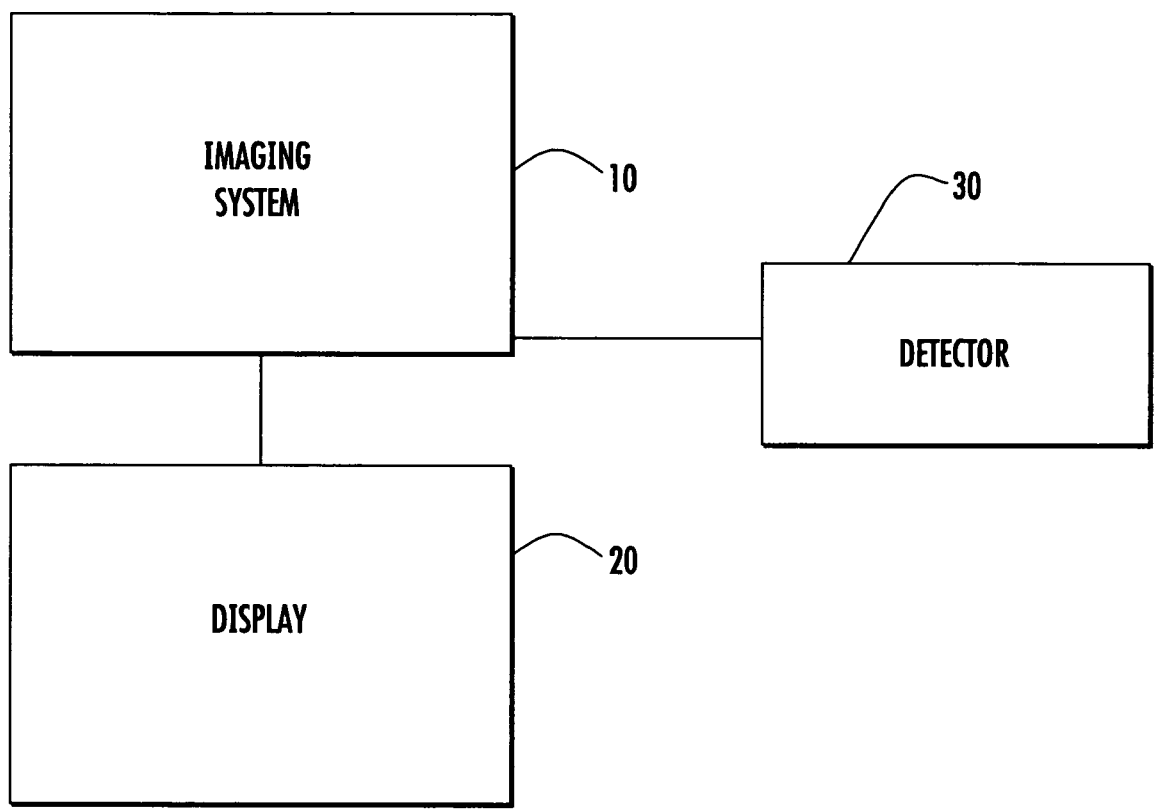
FIG. 1 illustrates an exemplary diagnostic imaging system.

FIG. 1 illustrates an imaging system 10 with an associated display 20. Imaging system 10 can be of any modality, but in one embodiment, system 10 is a CT system. In another embodiment, system 10 is a dual modality imaging system such as a combined CT/PET system and data processing can be done in one modality (e.g., CT) and the processed data can be transferred to the other modality (e.g., PET). Display 20 can be separate from system 10 or integrated with system 10. System 10 includes an acquisition device such as an x-ray radiation detector 30. X-ray detector 30 can be separate from system 10 or integrated with system 10.

The x-ray imaging system includes a processing circuit. The processing circuit (e.g., a microcontroller, microprocessor, custom ASIC, or the like) is coupled to a memory and a display device. The memory (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device such as display 20. In one embodiment, the processing circuit executes instructions stored in firmware (not shown).

Of course, the methods described herein are not limited to practice in system 10 and can be utilized in connection with many other types and variations of imaging systems. In one embodiment, the processing circuit is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

This disclosure describes an improvement to current CT scanners with a detector design for improved Standard Cardiac CT or EDCT Cardiac CT Imaging. One embodiment uses a known Cardiac digital projection 2D array (for example, a Revolution™ XR/d detector commercially available from the GE Healthcare business of the General Electric Company, or another digital projection radiographic detector, hereinafter "DPR detector") in the center of the current CT detector. This would generate a design similar to the Chevy emblem shape that reduces overall cost, as compared to a large coverage in Z (patient axis) detector across the entire field of view. In general, the DPR detector is not well suited for use in a CT system for performing general scans, because the DPR detector has limited dynamic range and longer lag or afterglow than the existing CT detectors. However, when the DPR detector is used in the center of the CT detector, these concerns are greatly lessened and the DPR detector has the resolution desired in Cardiac imaging. Advanced calibration and corrections are also available for the DPR detector. Sampling speed may also not be as big an issue in the center of the CT image along with recent improvements in DPR detectors. The DPR detector could be double stacked in the x-ray penetration direction, possibly along with a notch x-ray filter for energy discrimination computed tomography (EDCT) applications. This is because the DPR detectors pass high-energy x-rays. Therefore, the lower energy x-rays would impinge the first detector and be absorbed while the high-energy x-rays would pass through the first detector, and impinge a second detector, being absorbed by the second detector. This double stacking could also mitigate dynamic range concerns because the effective system dynamic range will be approximately double the dynamic range of a single DPR detector. By notch x-ray filter, it is meant any x-ray attenuating material, which would provide for a greater energy separation between the higher energy x-rays, and the lower energy x-rays. And as used herein, the expression "a notch filter operationally coupled to a detector" or similar language means that the filter is positioned such that x-rays impinge both the filter and the detector. The filter could be positioned between the X-ray tube and the patient or between detector 1 and detector 2 in the x-ray penetration direction.

Figure 2:
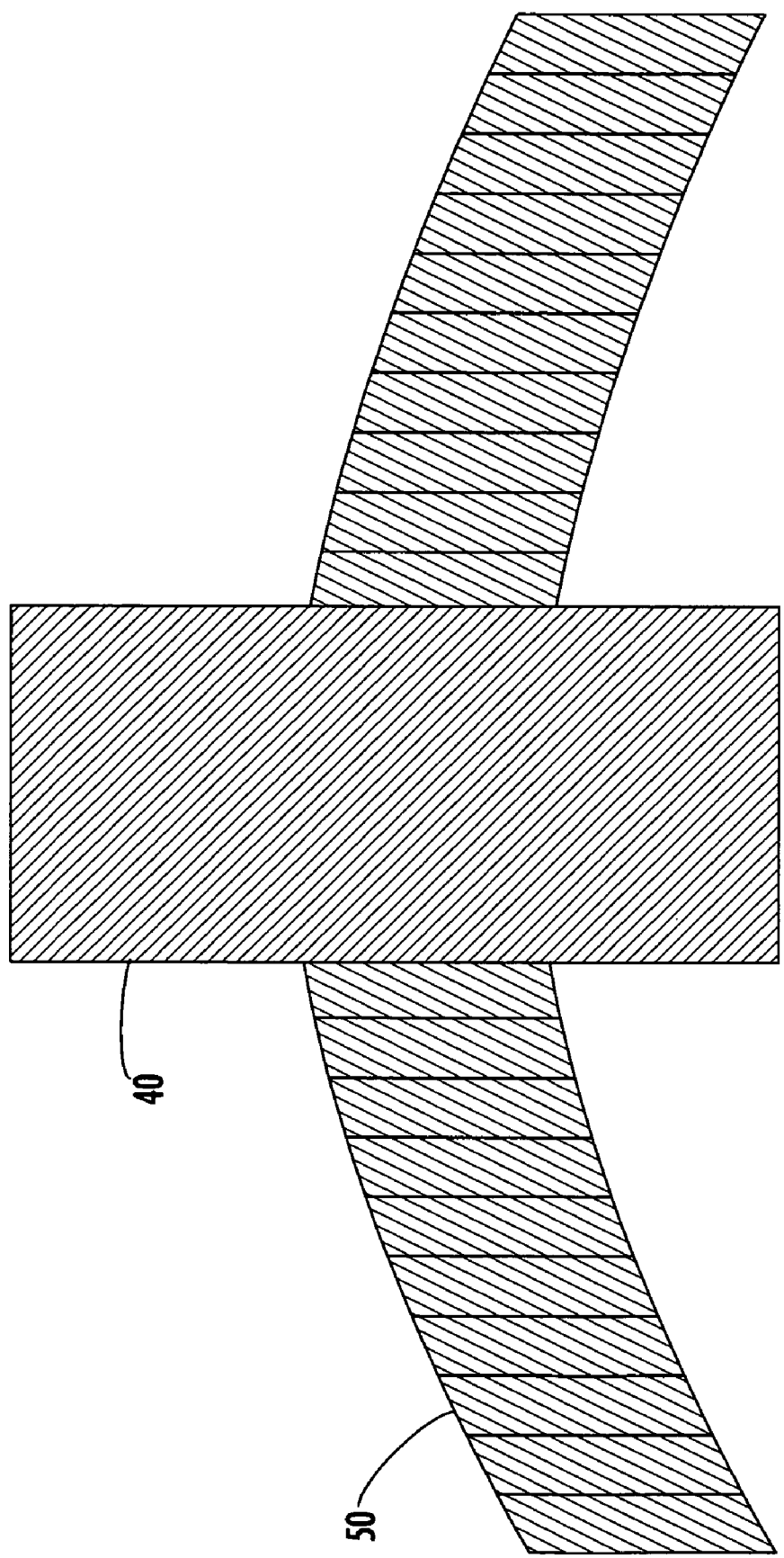
FIG. 2 illustrates the known curvilinear detector and the known Revolution™ XR/d detector forming a new combination.

FIG. 2 illustrates the known curvilinear detector 50 and the known DPR detector 40 forming a new combination. Note that the width of each module of the known curvilinear detector is approximately 4 cm while the width of the DPR detector is approximately 20 cm. During a cardiac scan, because the width is 20 cm, the whole heart may be scanned during a single rotation of the CT gantry. In one embodiment, the DPR detector is movably mounted and may be moved from being in front of curvilinear detector 50 such that a normal scan may be generated. Additionally, the known DPR detector can be easily adapted to be configured to be connected to the known curvilinear detector, and as such existing CT scanners can be retrofitted such of the herein described methods and apparatus are enabled.

Technical effects include that the herein described methods and apparatus provide for the whole heart being scanned during a single rotation of the CT gantry. The herein described methods and apparatus provide for reduced cost, larger coverage, EDCT imaging, and high resolution. The herein described methods and apparatus are useful for cardiac imaging, and allow for a quick new product introduction.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. An apparatus comprising:
a curvilinear computed tomography detector having a first portion and a second portion; and
a non-curvilinear computed tomography detector aligned between the first portion and the second portion of the curvilinear computed tomography detector; and
wherein the curvilinear computed tomography detector is configured to receive non-heart data and the non-curvilinear computed tomography detector is configured to receive heart data.

2. An apparatus in accordance with claim 1 wherein the non-curvilinear computed tomography detector is flat.

3. An apparatus in accordance with claim 1 wherein the non-curvilinear computed tomography detector and the curvilinear computed tomography detector have different dynamic ranges.

4. An apparatus in accordance with claim 3 wherein the non-curvilinear computed tomography detector and the curvilinear computed tomography detector having different afterglow attributes.

5. An apparatus in accordance with claim 1 wherein the non-curvilinear computed tomography detector and the curvilinear computed tomography detector having different afterglow attributes.

6. An apparatus in accordance with claim 1 wherein the first computed tomography detector comprises a digital projection radiographic detector.

7. An apparatus in accordance with claim 1 wherein the first computed tomography detector has a resolution for cardiac imaging.

8. A system comprising:
an x-ray source;
a first x-ray detector positioned to receive x-rays emitted from the x-ray source representing non-heart data; and
a second x-ray detector positioned to receive x-rays emitted from the x-ray source representing heart data, wherein the second x-ray detector is positioned with respect to the first x-ray detector such that the second x-ray detector at least partially blocks x-rays from impinging the first x-ray detector.

9. A system in accordance with claim 8 wherein the first x-ray detector is substantially centered with respect to the second x-ray detector.

10. A system in accordance with claim 8 wherein the first x-ray detector comprises a digital projection radiographic detector.

11. A system in accordance with claim 8 wherein the second x-ray detector comprises a curvilinear detector.

12. A method of manufacturing comprising:
providing a first detector for receiving heart data;
providing a second detector for receiving non-heart data, wherein the second detector is different than the first detector; and
arranging the first and second detectors with respect to an x-ray source such that x-rays emitted from the x-ray source impinge the first and second detectors.

13. A method in accordance with claim 12 wherein the first detector has a width of about 20 cm the second detector has a width of about 4 cm.

14. A method in accordance with claim 12 wherein the first and second detectors are configured such that heart data is received during a single rotation of a CT gantry.

* * * * *